United States Patent
Bair

Patent Number: 5,853,384
Date of Patent: Dec. 29, 1998

[54] FLUID JET SURGICAL CUTTING TOOL AND ASPIRATION DEVICE

[75] Inventor: Scott Bair, Atlanta, Ga.

[73] Assignee: SurgiJet, Inc., Orinda, Calif.

[21] Appl. No.: 436,138

[22] Filed: May 8, 1995

Related U.S. Application Data

[63] Continuation-in-part of Ser. No. 438,905, May 10, 1995, Pat. No. 5,562,692, which is a continuation-in-part of Ser. No. 96,297, Jul. 26, 1993.

[51] Int. Cl.$^6$ ................................................. A61B 17/20
[52] U.S. Cl. ........................... 604/22; 604/141; 604/143
[58] Field of Search ............................. 604/22, 23, 140, 604/141, 143, 146, 147, 313, 315, 316

[56] References Cited

U.S. PATENT DOCUMENTS

| | | |
|---|---|---|
| Re. 33,258 | 7/1990 | Onik et al. ............................. 604/22 |
| 3,353,537 | 11/1967 | Knox et al. . |
| 3,452,745 | 7/1969 | Hutchinson et al. . |
| 3,515,130 | 6/1970 | Tsujino . |
| 3,542,017 | 11/1970 | Adams . |
| 3,561,433 | 2/1971 | Kovach . |
| 3,605,745 | 9/1971 | Hodosh . |
| 3,768,472 | 10/1973 | Hodosh et al. . |
| 3,792,701 | 2/1974 | Kloz et al. . |
| 3,811,795 | 5/1974 | Olsen . |
| 3,906,954 | 9/1975 | Baehr et al. . |
| 3,930,505 | 1/1976 | Wallach . |
| 3,994,297 | 11/1976 | Kopf . |
| 4,018,623 | 4/1977 | Walker . |
| 4,278,078 | 7/1981 | Smith . |
| 4,282,867 | 8/1981 | DuToit . |
| 4,319,570 | 3/1982 | Grane ............................. 604/147 X |
| 4,365,752 | 12/1982 | Waisbren et al. . |
| 4,412,823 | 11/1983 | Sakai et al. . |
| 4,515,532 | 5/1985 | Walling . |
| 4,534,340 | 8/1985 | Kerr et al. . |
| 4,560,373 | 12/1985 | Sugino et al. . |
| 4,561,856 | 12/1985 | Cochran . |
| 4,570,632 | 2/1986 | Woods . |
| 4,583,531 | 4/1986 | Mattchen . |
| 4,589,412 | 5/1986 | Kensey . |
| 4,655,197 | 4/1987 | Atkinson . |
| 4,690,672 | 9/1987 | Veltrup . |
| 4,705,500 | 11/1987 | Reimels et al. . |
| 4,764,165 | 8/1988 | Reimels et al. . |
| 4,776,840 | 10/1988 | Freitas et al. . |
| 4,790,824 | 12/1988 | Morrow et al. . |

(List continued on next page.)

FOREIGN PATENT DOCUMENTS

| | | |
|---|---|---|
| 6275086 | 9/1986 | Australia . |
| 0175096 | 7/1985 | European Pat. Off. . |
| 0253478 | 1/1988 | European Pat. Off. . |
| 0356372 | 2/1990 | European Pat. Off. . |
| 0411170 | 2/1991 | European Pat. Off. . |
| 8706455 | 11/1987 | WIPO . |

OTHER PUBLICATIONS

Vijay, "A Critical Examination of the Use of Water Jets for Medical Applications", 5th American Water Jet Conference, Aug. 29–31, 1989: Toronto, Canada.

Uchino et al., "Surgical Cutting of the Liver by Water Jet" 9th International Symposium on Jet Cutting Technology, Sendai, Japan: 4–6 Oct., 1988.

*Primary Examiner*—Michael Buiz
*Assistant Examiner*—A. T. Nguyen
*Attorney, Agent, or Firm*—Harris Zimmerman

[57] ABSTRACT

An instrument for providing high pressure fluid pulses for cutting tissue including an internal pressure intensifying mechanism, and the provision of a suction force at the distal end of the instrument including an internal vacuum generating device to increase the suction force provided by a conventional suction source. A piston mechanism is provided for converting a low pressure fluid input to a high pressure fluid output, and a second piston mechanism is provided to intensify the suction force created by a conventional suction source at the surgical site.

13 Claims, 10 Drawing Sheets

U.S. PATENT DOCUMENTS

| | | | |
|---|---|---|---|
| 4,795,448 | 1/1989 | Stacey et al. | 604/319 |
| 4,817,599 | 4/1989 | Drews . | |
| 4,861,340 | 8/1989 | Smith et al. . | |
| 4,898,574 | 2/1990 | Uchiyana et al. . | |
| 4,913,698 | 4/1990 | Ito et al. . | |
| 4,921,476 | 5/1990 | Wuchinich | 604/22 |
| 4,944,726 | 7/1990 | Hilal et al. . | |
| 4,950,238 | 8/1990 | Sullivan . | |
| 5,019,037 | 5/1991 | Wang et al. . | |
| 5,033,961 | 7/1991 | Kandler et al. . | |
| 5,037,431 | 8/1991 | Summers et al. . | |
| 5,046,486 | 9/1991 | Grulke et al. | 601/161 |
| 5,049,124 | 9/1991 | Bales, Jr. . | |
| 5,064,413 | 11/1991 | McKinnon et al. . | |
| 5,135,482 | 8/1992 | Weracher . | |
| 5,135,484 | 8/1992 | Wright . | |
| 5,176,645 | 1/1993 | Guerrero . | |
| 5,218,956 | 6/1993 | Handler et al. . | |
| 5,441,482 | 8/1995 | Clague et al. | 604/35 |
| 5,562,692 | 10/1996 | Bair | 606/167 |
| 5,591,184 | 1/1997 | McDonnell et al. | 606/167 |

FLUID JET SURGICAL CUTTING TOOL AND ASPIRATION DEVICE

CROSS-REFERENCE TO RELATED APPLICATIONS

This application is a continuation-in-part of application Ser. No. 08/438,905, filed May 10, 1995, U.S. Pat. No. 5,562,692, which is a continuation of Ser. No. 08/096,297 filed Jul. 26, 1993, abandoned, the contents of which are incorporated herein by reference.

BACKGROUND OF THE INVENTION

1. Field of the Invention

The present disclosure generally relates to surgical cutting tools, and, more particularly, to cutting tools employing a fluid jet as the active cutting agent. The disclosure further relates to surgical cutting tools utilizing suction for aspiration purposes, and, in particular, relates to a tool for amplifying the suction force at the surgical site.

2. Discussion of the Prior Art

There is currently a great amount of interest in new technologies to replace or supplant traditional surgical cutting tools such as the scalpel. Laser-based tools, electrosurgical cutters, plasma jets, and fluid jets have all been introduced to improve various surgical and medical procedures. Each technology has advantages for particular procedures, as well as intrinsic drawbacks. Fluid jet cutters have several characteristics that make it an attractive new technology. For example, pulsed fluid jet cutters involve no electrical current or voltage, which can present a safety risk factor in delicate surgeries. Likewise, there is no heat generated by fluid jets. Indeed, fluid jets are inherently self-cooling. Also, the effects of pulsed fluid jets can be extremely localized and directional, unlike electrosurgical tools and some laser instruments.

Moreover, fluid jet cutters excel at removing soft tissue, due to the fact that high pressure pulsed jets tend to emulsify soft tissue, and the emulsified tissue is easily transported by aspiration away from the surgical site. In contrast, competing technologies such as laser cutters and electrosurgical cutters remove tissue by ablation or electrothermal dissolution.

Indeed, the fact that fluid jet cutting devices include aspiration and evacuation as an integral portion of the device is an added benefit for many surgical procedures. Surgical cutting and excision often involves exsanguination that occludes the surgical field, and the surgeon must employ an assistant to aspirate the field to permit adequate visualization. Fluid jet devices that aspirate the fluid and emulsified tissue also remove the blood and other fluids that might otherwise affect visualization by the surgeon, and they do so without involving additional personnel.

However, fluid jet devices known in the prior art exhibit some negative characteristics that limit their usefulness. Within restricted body cavities and organs, the volume of the fluid introduced by the cutting instrument may exceed the aspiration ability of the instrument, resulting in distention and expansion that can have deleterious side effects. The emulsification effect is primarily a consequence of pulsing the high pressure fluid jet, and the pulse parameters are critical in efficiently emulsifying tissue. Generally speaking, prior art fluid jet tools have not been capable of achieving sufficiently short, well-defined pulses of high pressure fluid to emulsify tissue effectively and completely. Any portion of a fluid pulse that is not delivered at high pressure is ineffective, and merely adds fluid to the surgical field. As a result, a greater volume of fluid is consumed for a given cutting or excision procedure, requiring more time for the surgeon and the provision of more robust aspiration capabilities in the tool.

As a safety measure, it is critical that any fluid jet cutting tool be prevented from emitting a steady stream of high pressure fluid, which can quickly penetrate deeply into soft tissue and can cause catastrophic damage. Some prior art pulsed fluid jet instruments are not designed to inherently prevent a high pressure stream, and must be carefully controlled by external devices to avoid serious accidents.

In addition, many devices in the prior art provide for connection to a source of suction to permit the surgeon to aspirate the excess fluid from the surgical site utilizing the single instrument. These devices provide a constant suction force, which is disadvantageous in that many times a greater or lesser suction force may be desirable. It may be necessary to interrupt the surgical procedure to adjust the suction force at the source which, usually, is remote from the instrument. Typically, these instruments only provide for activating and deactivating the suction force not for adjusting or modifying the level of force.

Furthermore, in the event that the aspiration or suction cannula of a conventional device becomes clogged with emulsified tissue or the like, manual cleaning of the cannula tip is required, thus, necessitating an interruption of the surgical procedure to permit surgical personnel to clear the blockage. This can be disadvantageous to the patient, particularly for those undergoing procedures such as cataract surgery or the like. Removing the instrument for cleaning during cataract surgery at the very least requires second entry puncture to the eye capsule. Even further, the emulsified tissue which clogs the cannula tip and fails to enter the aspiration cannula will cause an increase in suction within the instrument. The increase in suction will result at the very least in a reduced internal volume of the flexible hose connecting the suction source with the aspiration cannula and possible breakdown of the system.

Thus, a need exists for a fluid jet cutting instrument having aspiration capabilities, which provides for a variation in the force of the suction and which permits for automatic clearing of the instrument in the event of a blockage.

SUMMARY OF THE INVENTION

The present disclosure generally relates to a pulsed fluid jet instrument for surgical cutting and excision. The instrument features superior pulse characteristics which optimize cutting and emulsification while minimizing the amount of fluid used in the process and preventing the emission of a steady stream of high pressure fluid into tissue.

In a preferred embodiment, the instrument includes a handpiece, a cannula extending from a handpiece and having an inner needle designed to emit a pulsed fluid jet for cutting and emulsification purposes and an outer concentric needle or tube connected to a negative pressure source for aspiration and evacuation of the fluid and tissue. The handpiece features a pressure intensifier piston arrangement that receives fluid at relatively low pressure. The piston arrangement operates reciprocally and reiteratively to pump the fluid through the jet needle in a series of high pressure pulses, each having a nearly rectangular pressure waveform.

The pressure intensifier piston is preferably T-shaped having a broad end which divides a drive bore into an actuating chamber and a retracting chamber. A bistable valve is connected to admit high pressure gas into the actuating chamber, thereby driving the piston to translate. The narrow end of the piston is disposed in a fluid pumping chamber which is connected to a supply of fluid. The translating piston drives the fluid from the pumping chamber through a first check valve into the fluid jet needle which directs the high pressure fluid pulse to a tissue target. Pressurized gas is admitted to the retracting chamber via the bistable valve, thereby driving the piston retrograde and allowing the pumping chamber to refill with fluid through a second check valve.

There is no high pressure fluid supplied to the handpiece. The pressure intensifying pumping action of the piston creates a high pressure fluid pulse. Moreover, the gas supply to drive the piston is at a relatively low pressure such that gas pressure cannot form a safety risk to the patient. Thus, failure of the piston mechanism will not result in the emission of a stream of high pressure fluid. Consequently, the instrument is inherently safer than prior art instruments which are connected to a high pressure fluid source.

Another feature of the present disclosure lies in the provision of an aspiration mechanism including a vacuum generating mechanism for increasing the suction force at the tip of the cannula portion of the instrument. The vacuum generating mechanism is disposed in the handle of the instrument and may be utilized to create a suction at the cannula tip, or, to supplement a constant suction source connected to the instrument. The vacuum generating mechanism includes a spring biased piston member which is disposed in the housing and separates the interior into at least a driving chamber and a suction chamber. Preferably, the end of the piston disposed in the suction chamber includes a sealing member, such as an O-ring or the like, which assists in creating the suction force. The suction chamber is positioned in-line between the cannula and the discharge port.

The driving chamber of the aspiration mechanism is connected to a low pressure gas source and has a venting port for venting the gas supplied from the gas source. As gas is charged to the driving chamber, pressure builds until the gas pressure overcomes the spring force, thereby driving the piston member into the suction chamber. The gas present in the driving chamber is then vented from the chamber through the vent port to permit the piston member to return to the driving chamber under the influence of the spring force. This returning movement of the piston in conjunction with the sealing ring creates a suction force in the cannula for aspiration purposes. The charging and venting of the gas from the driving chamber is repeated as desired either in a continuous mode or in an intermittent mode. The vacuum generating mechanism may be provided by itself, or, may be utilized to supplement and enhance a continuous, remote suction source coupled to the instrument. The vacuum generating mechanism may also be provided in an instrument for aspiration only, or may be provided in an instrument having irrigation or fluid jet cutting capabilities.

BRIEF DESCRIPTION OF THE DRAWINGS

So that one skilled in the art to which the subject disclosure appertains will better understand how to make and use the disclosure, preferred embodiments of the surgical apparatus will be described hereinbelow with reference to the drawings wherein.

DESCRIPTION OF THE PREFERRED EMBODIMENTS

Figure 1:
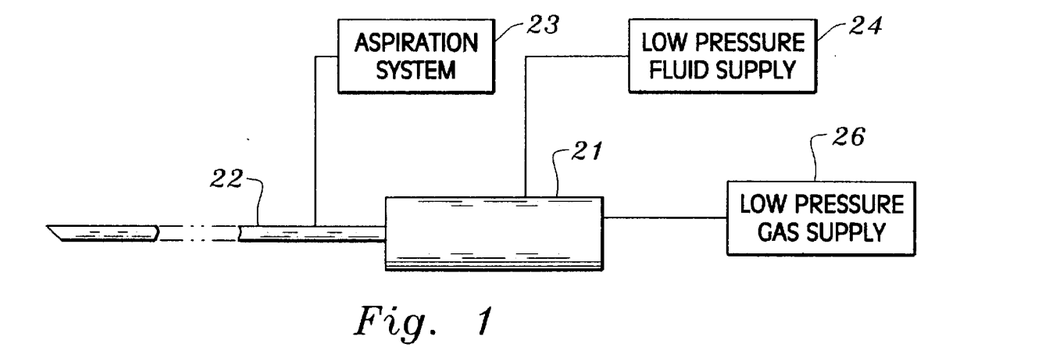
FIG. 1 is a functional block diagram of the fluid jet surgical instrument of the present disclosure.

The present disclosure generally includes a pulsed fluid jet surgical instrument for cutting, excision, emulsification and removal of tissue. With reference to FIG. 1, the instrument includes a handpiece 21 adapted to be wielded manually with a cannula 22 extending therefrom. Cannula 22 emits a pulsed jet of high pressure fluid for surgical cutting and tissue emulsification. Cannula 22 is connected to an aspiration system 23 which provides vacuum aspiration to remove the fluid introduced by the instrument, as well as body fluids and emulsified tissue. The handpiece 21 is also connected to a low pressure fluid supply 24 that provides the fluid which forms the high pressure pulsed cutting jet. A low pressure gas supply 26 is also connected to the handpiece 21 to power the handpiece to produce high pressure fluid pulses.

Figures 2, 6:
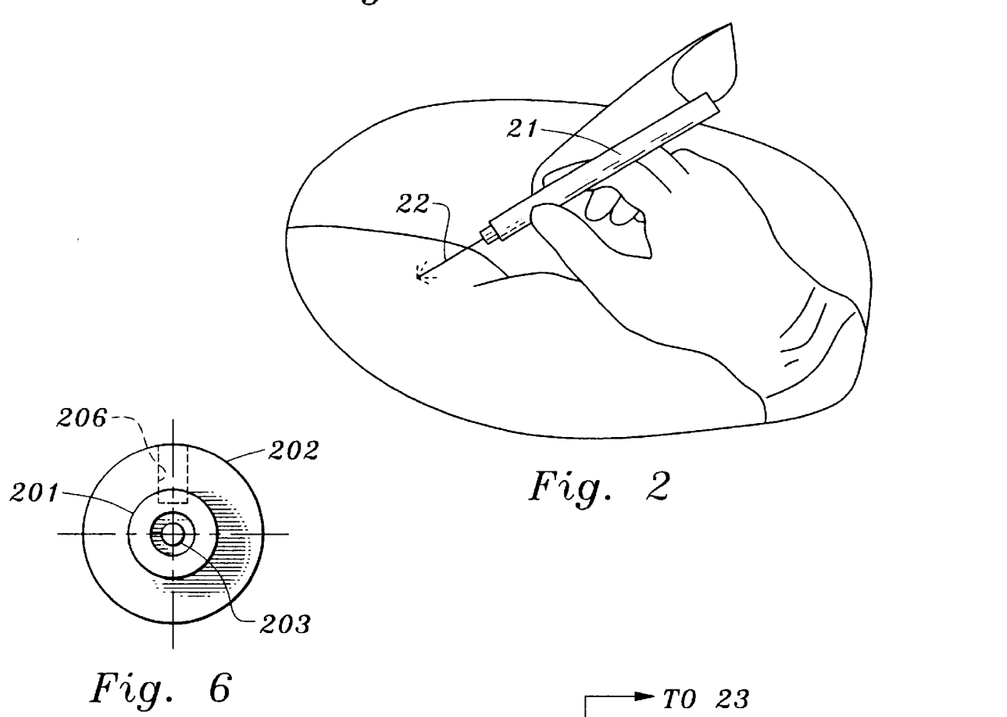
FIG. 2 is a perspective view showing the fluid jet surgical instrument in use.
FIG. 6 is an end view of the cannula portion of the fluid jet surgical instrument.

The instrument is wielded by a surgeon as shown in FIG. 2 to produce surgical cutting and excision tasks for therapeutic purposes. It should be noted initially that the handpiece 21 is devoid of any connection to a high pressure source of any kind. As a result, failure of the instrument will not introduce a high pressure fluid stream into the patient. Thus, the disclosure is inherently safer than conventional instruments utilizing fluid cutting capabilities.

Figure 3:
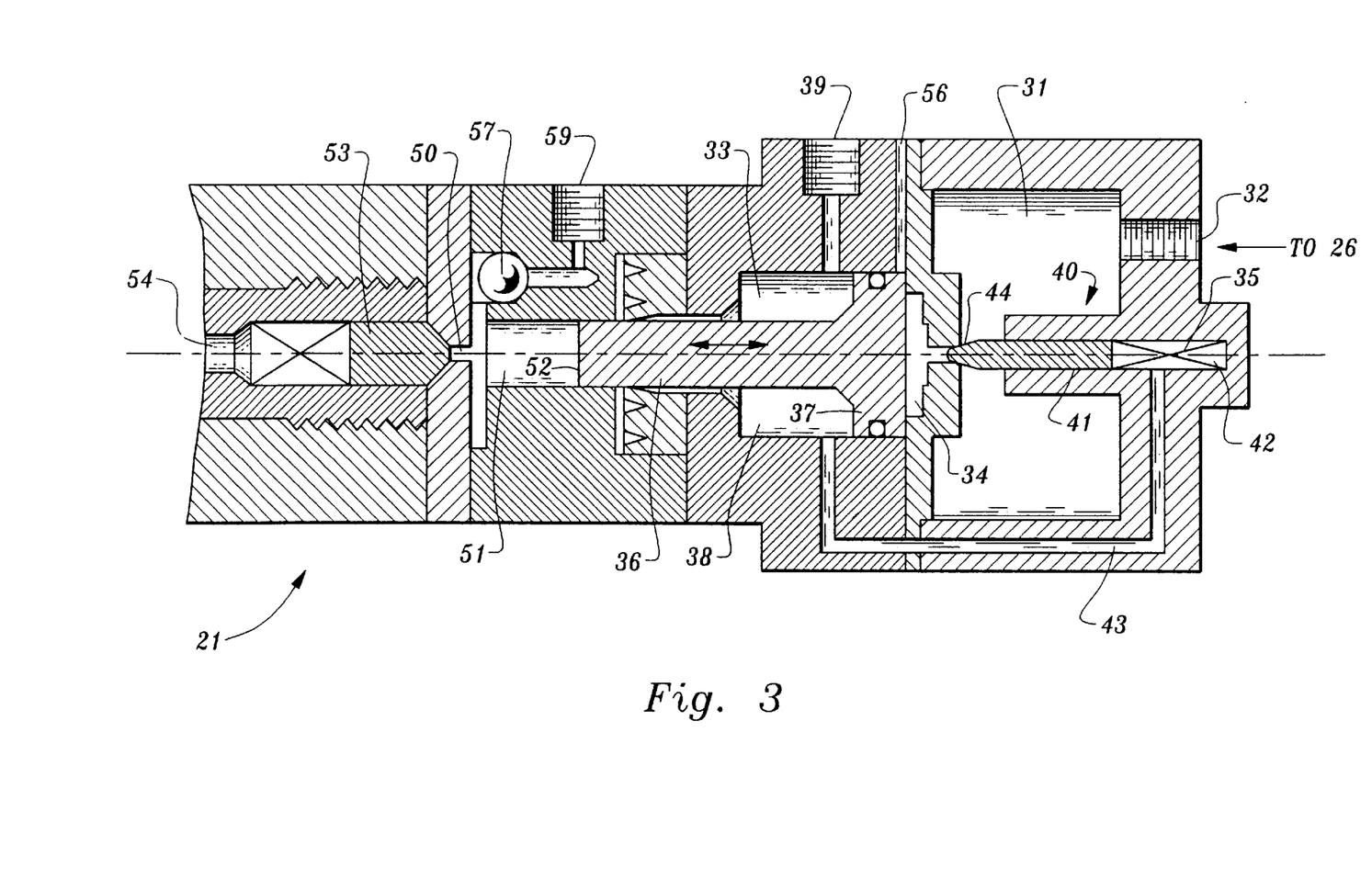
FIG. 3 is a cross-sectional view of the pressure intensifier portion of the fluid jet surgical instrument of the present disclosure.

With regard to FIG. 3, the handpiece 21 includes an interior gas reservoir 31 that is connected through port 32 to the low pressure gas supply 26. The handpiece also provides a piston 36 having a broad head 37 that is disposed concentrically in a bore 33 in a pressure sealing, translating fashion. The head 37 divides the bore 33 into a driving chamber 34 and a retracting chamber 38. The retracting chamber 38 communicates through port 39 to an actuating valve (not shown) that selectively vents the retracting chamber 38 and permits pulsed operation of the unit. The actuating valve may include a pneumatic switch on the handpiece, or a footswitch coupled by tubing to the port 39.

The handpiece further includes a bistable valve assembly 40 consisting of valve pintle 41 slidably disposed in a bore 42. Bore 42 is connected through passageway 43 to retracting chamber 38. A valve port 44 extends from the driving chamber 34 to the gas reservoir 31. The tip of valve pintle 41 seats in port 44 to selectively block gas flow from gas reservoir 31 to driving chamber 34. A compression spring (shown schematically as element 35) is disposed in the bore 42 to bias pintle 41 to close the port 44.

Piston 36 includes a narrow pumping end 52 disposed in a pump chamber 51. Pump chamber 51 communicates through an outlet passage 50 to a relief valve 53, which in turn leads to a tube 54 connected to the jet outlet port. The relief valve 53 is set to open at a relatively high pressure, so that no fluid flow is admitted to the jet outlet port until pressure in the pump chamber 51 attains a predetermined high value. With this arrangement, the jet pulses are comprised solely of high pressure fluid, and the pressure versus time profile of each pulse approaches a rectangular waveform. Fluid such as sterile saline solution, Ringer's solution, or the like is supplied to the pump chamber 51 from supply 24 through inlet port 59 and ball check valve 57.

To operate the apparatus depicted in FIG. 3, the actuating valve connected to port 39 is opened, venting the retracting chamber 38 to ambient pressure. The pressure in bore 42 likewise drops, due to the flow communication of passageway 43. Low pressure gas is supplied into gas reservoir 31 through port 32. When the gas pressure in reservoir 31 overcomes the spring force of spring 35 acting on the pintle 41, the pintle 41 is driven rearwardly into the bore 42, opening port 44 and admitting pressurized gas from the reservoir 31 into the driving chamber 34. As a result, piston 36 translates toward the jet tube 54, compressing the fluid in the pump chamber 51. When the pressure in the pump chamber 51 exceeds the threshold of the relief valve 53, fluid is expelled through the jet tube 54 as a high pressure fluid pulse.

It is significant to note that the driving surface of the piston head 37 is far greater in area than the pump end 52, and that the same force develops an intensified pressure thereby creating a very high pressure pulse on the order of ten times or more from a low pressure fluid supply and a low pressure gas supply. For example, fluid to pump chamber 51 may be provided at approximately 100 psig, and the relief valve may be set to open at 300 psig or more. The maximum pressure developed during the pressure pulse may exceed 1000 psig, even though the gas pressure supplied to the instrument may only be 100–120 psig.

When the actuating valve which is in communication with vent 39 is closed, gas pressure leaking past the pintle 41 and through the passageway 43 begins to build pressure in the retracting chamber 38. Pressure also builds in the bore 42, urging the pintle 41 to translate forwardly and seal the inlet port 44. Gas pressure bleeds from the driving chamber 34 through a bleed passage 56, and the piston 36 retracts. The relief valve 53 closes when the piston begins to retract, and inlet valve 57 opens to permit pump chamber 51 to refill. Thus, the high pressure fluid jet pulse is completed, and the apparatus is set to deliver another pulse. However, it should be noted that the actuating valve must be reopened to initiate another pulse, and that the mechanism is not free-running. Thus, there is no possibility of the instrument delivering additional pulses after shutdown is desired. Consequently, the apparatus is inherently safe in another important characteristic.

With regard to FIG. 4 and FIGS. 7–10, a further embodiment 121 of the handpiece is illustrated, which possesses enhanced manufacturing, cleaning, and servicing capabilities. The handpiece 121 includes an interior gas reservoir 131 that is connected through side port 132 to the low pressure gas supply 26. The handpiece includes a piston 136 having a broad head 137 that is disposed concentrically in a bore 133 in a pressure sealing, translating fashion. The head 137 divides the bore 133 into a driving chamber 134 and a retracting chamber 138. The retracting chamber 138 communicates through port 139 to an actuating valve 190 [FIG. 7] that selectively vents the retracting chamber 138 to permit pulsed operation of the unit. The actuating valve 190 may comprise a pneumatic switch on the handpiece, or a footswitch coupled by tubing to the port 139. If the actuating valve 190 is remote to the handpiece, an accumulator (not shown) and a restrictor (not shown) may be required to achieve correct timing. Preferably, the accumulator is added adjacent valve bore 142 and the restrictor is placed between valve bore 142 and actuating valve 190. A bleed port 156 extends from the driving chamber 134 to ambient air.

Figure 4:
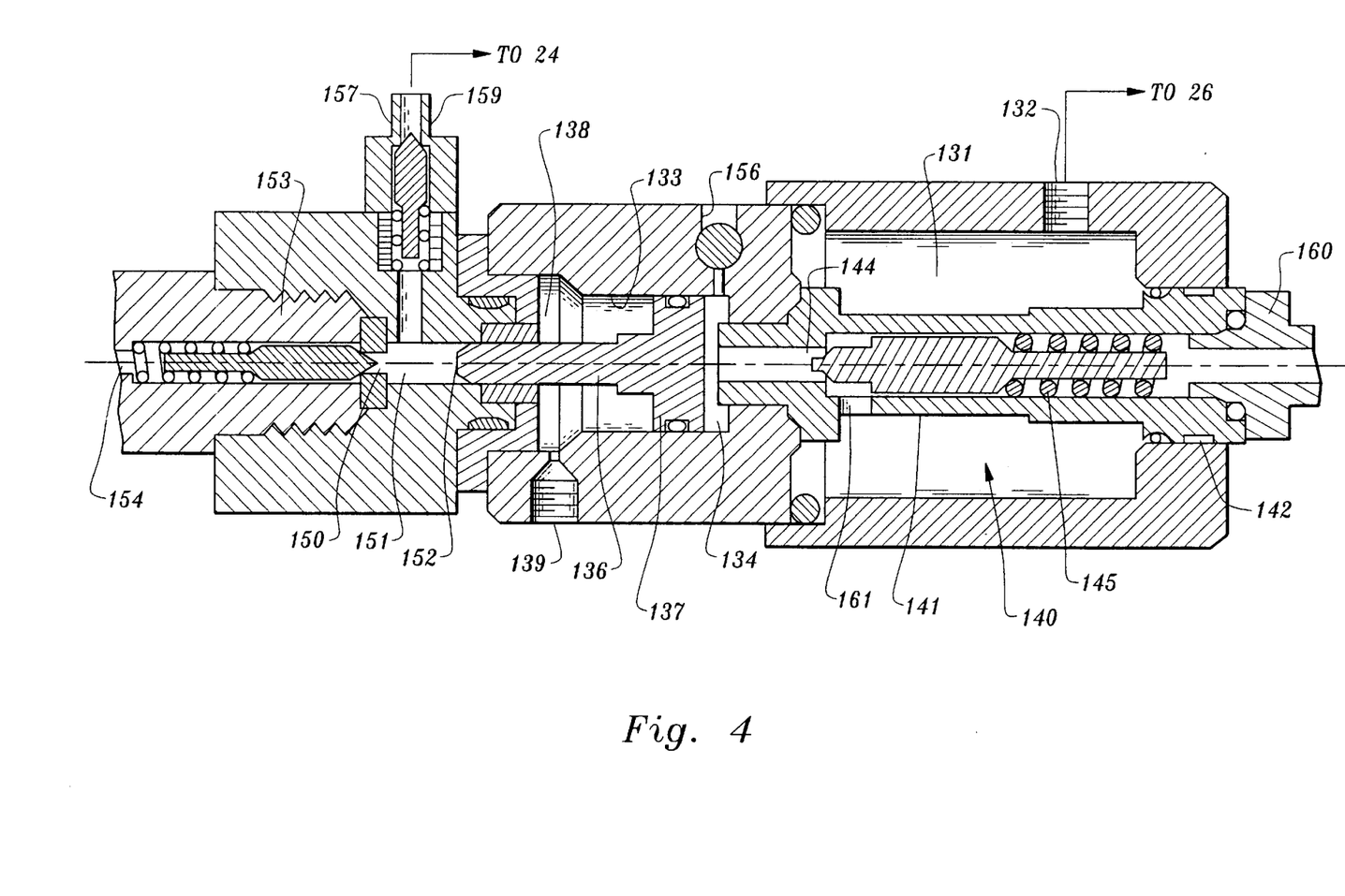
FIG. 4 is a cross-sectional view of another embodiment of the pressure intensifier portion of the fluid jet surgical instrument.

The handpiece further includes a bistable valve assembly 140, consisting of a valve pintle 141 slidably disposed in a bore 142. A valve port 144 extends from the driving chamber 134 through port 161 to the gas reservoir 131, and the tip of the valve pintle 141 seats in the port 144 to selectively block gas flow from the reservoir to the driving chamber 134. A compression spring 145 is disposed in the bore 142 to bias the pintle 141 to close the port 144. A connector 160 is coupled to the outer end of the bore 142, and is connected to join the bore 142 in flow communication with the port 139 of the retracting chamber 138.

The piston 136 includes a narrow pumping end 152 disposed in a pump chamber 151. The pump chamber 151 communicates through an outlet passage 150 to a relief valve 153, which in turn leads to a tube 154 connected to the jet outlet port. The relief valve 153 is set to open at a relatively high pressure, so that no fluid flow is admitted to the jet outlet port until pressure in the pump chamber attains a predetermined high value. With this arrangement, the jet pulses consist mostly of high pressure fluid, and the pressure versus time profile of each pulse approaches a rectangular waveform. Fluid such as sterile saline solution, Ringer's solution, or the like is supplied to the pump chamber from supply 24 through inlet port 159 and check valve 157.

Figure 9:
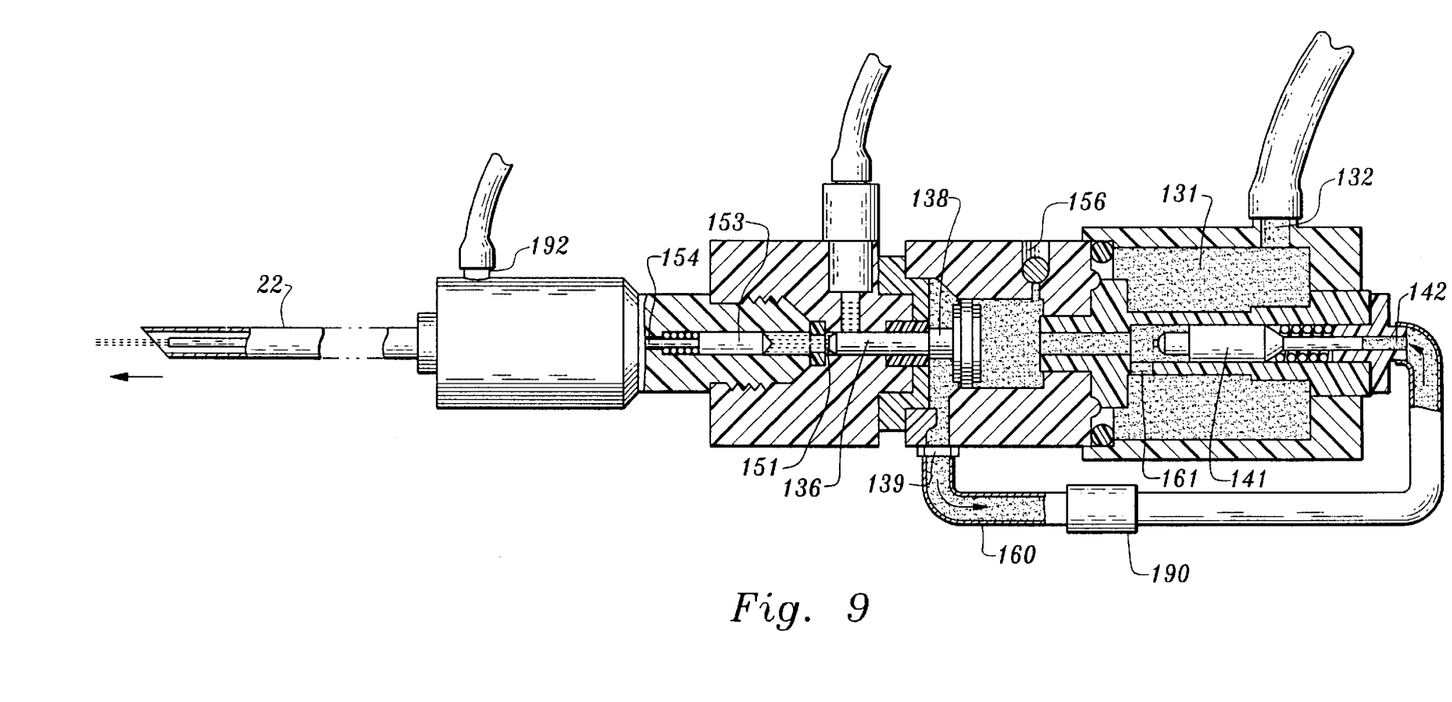
FIG. 9 is a cross-sectional view of the instrument of FIG. 7 as the fluid is ejected from the instrument.

To operate the apparatus 121, as best seen in the sequence of FIGS. 7–10, the actuating valve 190 connected to port 139 and 160 is opened, venting the retracting chamber 138 to ambient pressure. The pressure in bore 142 likewise drops, due to the flow connection between port 139 and connector 160. Gas introduced into gas reservoir 131 communicates through port 161. When the gas pressure overcomes the spring force of compression spring 145 acting on the pintle 141, the pintle 141 is driven into the bore 142 as shown by the directional arrow of FIG. 8, opening the port 144 and admitting pressurized gas from the reservoir 131 into the driving chamber 134. The piston 136 translates toward the jet tube 154 to compress the fluid in the pump chamber 151. When the pressure in the pump chamber 151 exceeds the threshold of the relief valve 153, fluid is expelled through the jet tube 154 as a high pressure fluid pulse, as shown in FIG. 9.

Figure 10:
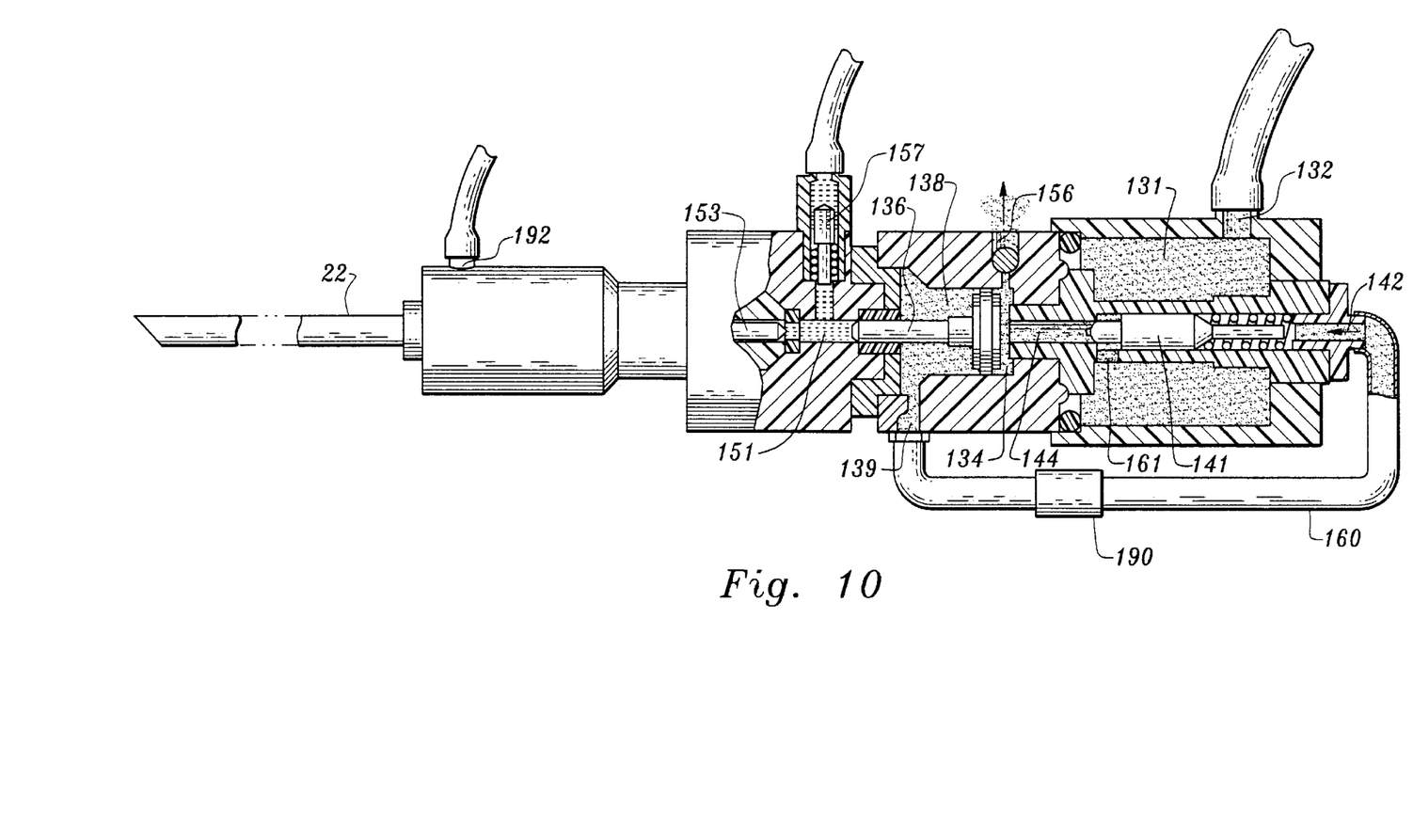
FIG. 10 is a cross-sectional view of the instrument of FIG. 7 as the pressure intensifier completes a stroke and is re-charged with fluid.

When the actuating valve 190 is closed, gas pressure leaking past the pintle 141 and through the connection to port .139 begins to build pressure in the retracting chamber 138. Pressure also builds in the bore 142, allowing the spring 145 to urge the pintle 141 to translate and seal the inlet port 144 as shown in FIG. 10. Gas pressure bleeds from the driving chamber 134 through the bleed passage 156, and the relatively higher pressure in the retracting chamber 138 causes the piston 136 to retract. The relief valve 153 closes when the piston begins to retract, and inlet valve 157 opens to permit the pump chamber to refill returning the apparatus to the position shown in FIG. 7. Thus one high pressure fluid jet pulse is completed, and the apparatus is set to deliver another pulse. As in the previous embodiment, the actuating valve 190 must be reopened to initiate another pulse, and the mechanism is not free-running. Thus there is no possibility of the apparatus delivering additional pulses after shutoff is desired.

Figure 5:
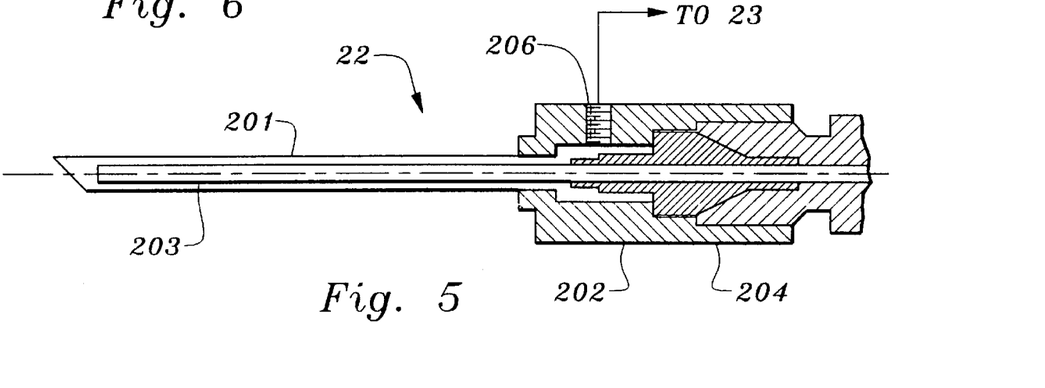
FIG. 5 is a cross-sectional view of the cannula portion of the fluid jet surgical instrument.

Referring now to FIGS. 5 and 6, the cannula assembly 22 of the fluid jet cutting instrument includes an aspiration tube 201 extending coaxially and distally from a housing 202. A jet tube 203 is disposed concentrically and coaxially within the aspiration tube 201, and is supported by a mandrel 204 secured within the housing 202. The distal end of the jet tube 203 is recessed slightly within the distal end of the aspiration tube, and the proximal end of the jet tube 203 is connected to the high pressure pulse output 54 (embodiment of FIG. 1) or 154 (FIG. 4) described previously. The interior of the housing 202 communicates with the interior space of the aspiration tube 201, and port 206 connects the aspiration tube to the aspiration system 23 described previously. The housing 202 is joined to either of the handpieces 21 or 121 described above.

The distal end of the jet tube 203 emits a train of pulses of high pressure fluid from the handpiece apparatus, causing the target tissue to be cut and emulsified. The suction provided by the aspiration tube removes the fluid emitted by the jet tube, as well as the emulsified tissue and body fluids, so that surgical cutting and tissue excision and removal may be carried out quickly and efficiently.

Figure 11:
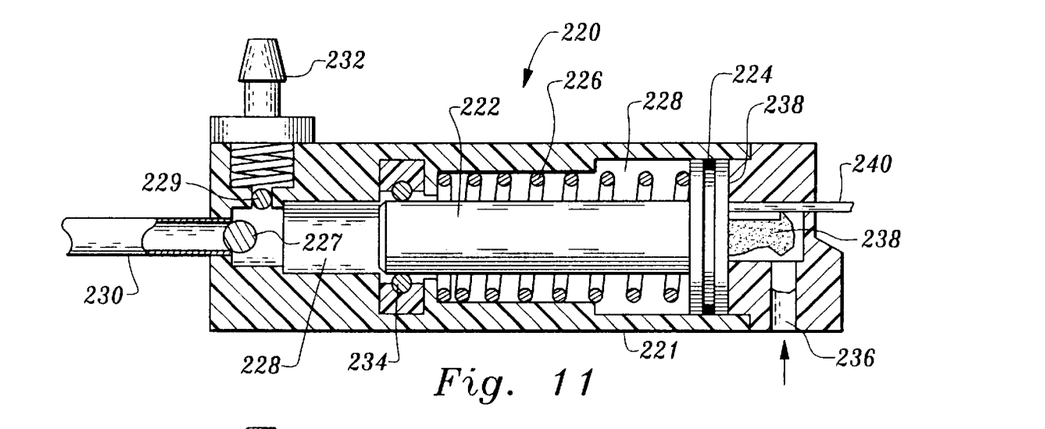
FIG. 11 is a cross-sectional view of a suction device of the present disclosure in an at rest condition.
Figure 12:
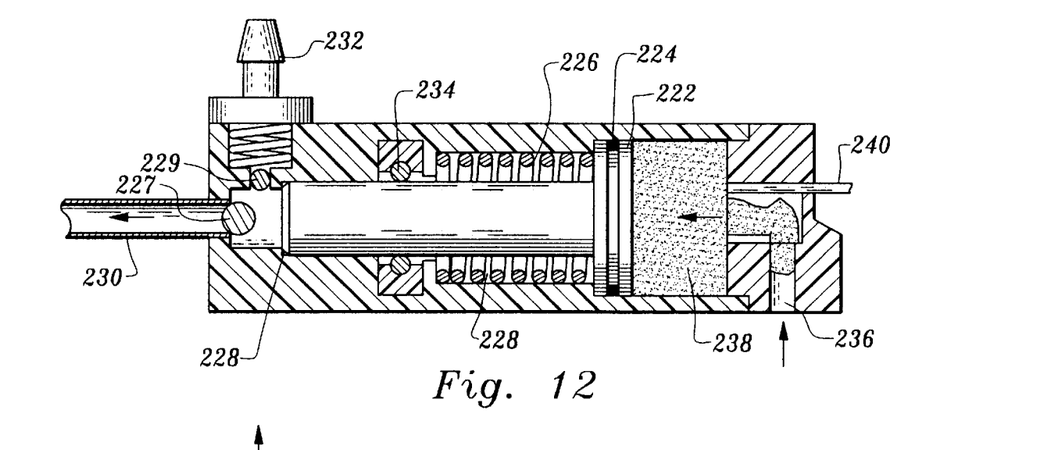
FIG. 12 is a cross-sectional view of the device of FIG. 11 in an operational mode.

Referring now to FIGS. 11 and 12, there is illustrated a suction device utilized for suction of fluids and emulsified tissue at the surgical site. Suction device 220 can be utilized as a stand alone device or may be incorporated into a handpiece such as in the handpiece 121 illustrated in FIGS. 4 and 7–10 as will be described in detail below. Suction device 220 includes a housing 221 which incorporates a piston member 222 for creating an increased suction force at the distal end of the unit illustrated as tube 230. Piston member 222 is similar to piston 136 as described above and includes a sealing member such as O-ring 224 to prevent the passage of gaseous fluid. Piston 222 is positioned in a central bore of housing 221 and separates the central bore into a suction chamber 228 and a drive chamber 238. Piston member 222 is spring biased to the position shown in FIG. 11 by spring member 226. The distal end of piston member 222 is further provided with a sealing device such as O-ring 234. Suction device 220 may be used to create a suction force at the distal end of tube 230, or may be used to supplement a conventional, constant suction source external to the instrument which may be connected to the instrument at suction port 232. Drive chamber 238 is supplied with gas through gas port 236 and includes a vent port 240 whose function will also be described below.

Figure 13:
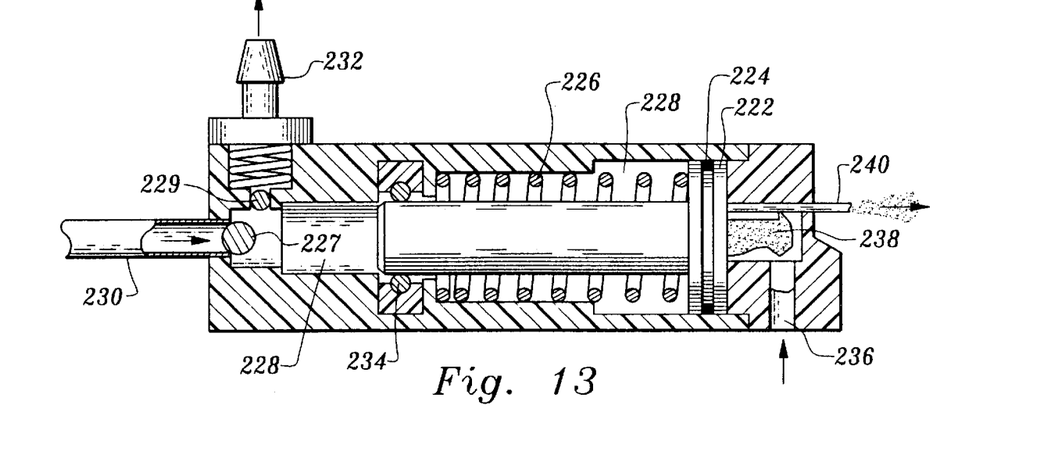
FIG. 13 is a cross-section view of the device of FIG. 11 illustrating the piston moved to its retracted position to create a suction force.

Suction device 220 will first be described for intensifying the conventional, constant suction source connected to the device at suction port 232. As is known, the external or remote suction source provides a constant suction force at the distal end of tube 230. In order to intensify the suction force, gas is supplied through gas port 236 to drive chamber 238, until the pressure within drive chamber 238 builds to a point where it overcomes the biasing force of spring 226. Once the biasing force of the spring 226 is overcome, piston 222 translates into suction chamber 228. As can be appreciated, the initial force of the piston 222 being driven into suction chamber 228 has the potential of creating a negative force of air through tube 230 and suction port 232. However, check valves 227, 229 prevent this from occurring. After piston 222 translates to the position shown in FIG. 12, vent port 240 is opened to release the gas pressure in drive chamber 238. As the pressure drops in drive chamber 238, the biasing force of spring 226 drives the piston back to the position shown in FIG. 13. As the piston moves in the direction of drive chamber 238, it creates a vacuum or suction force in suction chamber 228 via the O-ring 234 so as to enhance the suction force provided by the remote suction source in tube 230. Once the retraction stroke is completed and the device is in the position shown in FIG. 13, vent 240 is closed to allow the gas supply to charge the drive chamber 238 to translate the piston 222 to the position shown in FIG. 12 to repeat the suction stroke. This procedure is continued for as long as the increased suction is desired.

Suction device 220 may also be utilized as a stand alone instrument, in which suction is created by the reciprocating movement of piston 222, without connection to a conventional remote suction source. In this case, suction port 232 is connected to tubing which provides for drainage, so that as a suction force is created by the reciprocal movement of the piston, the emulsified tissue and excess fluid is drained through the tube connected to port 232.

Figure 7:
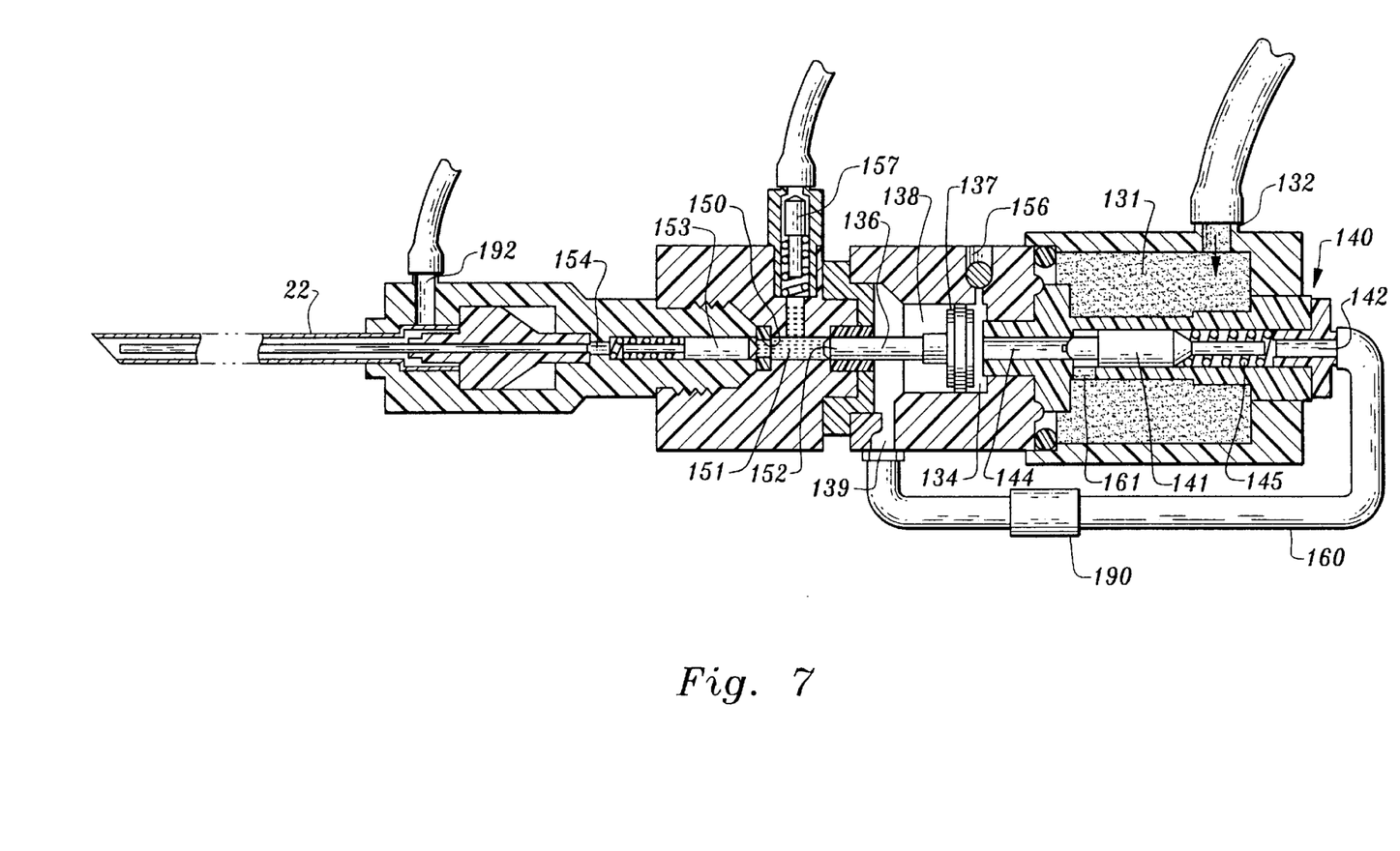
FIG. 7 is a cross-sectional view of the instrument of FIG. 4 in an at rest position.
Figure 8:
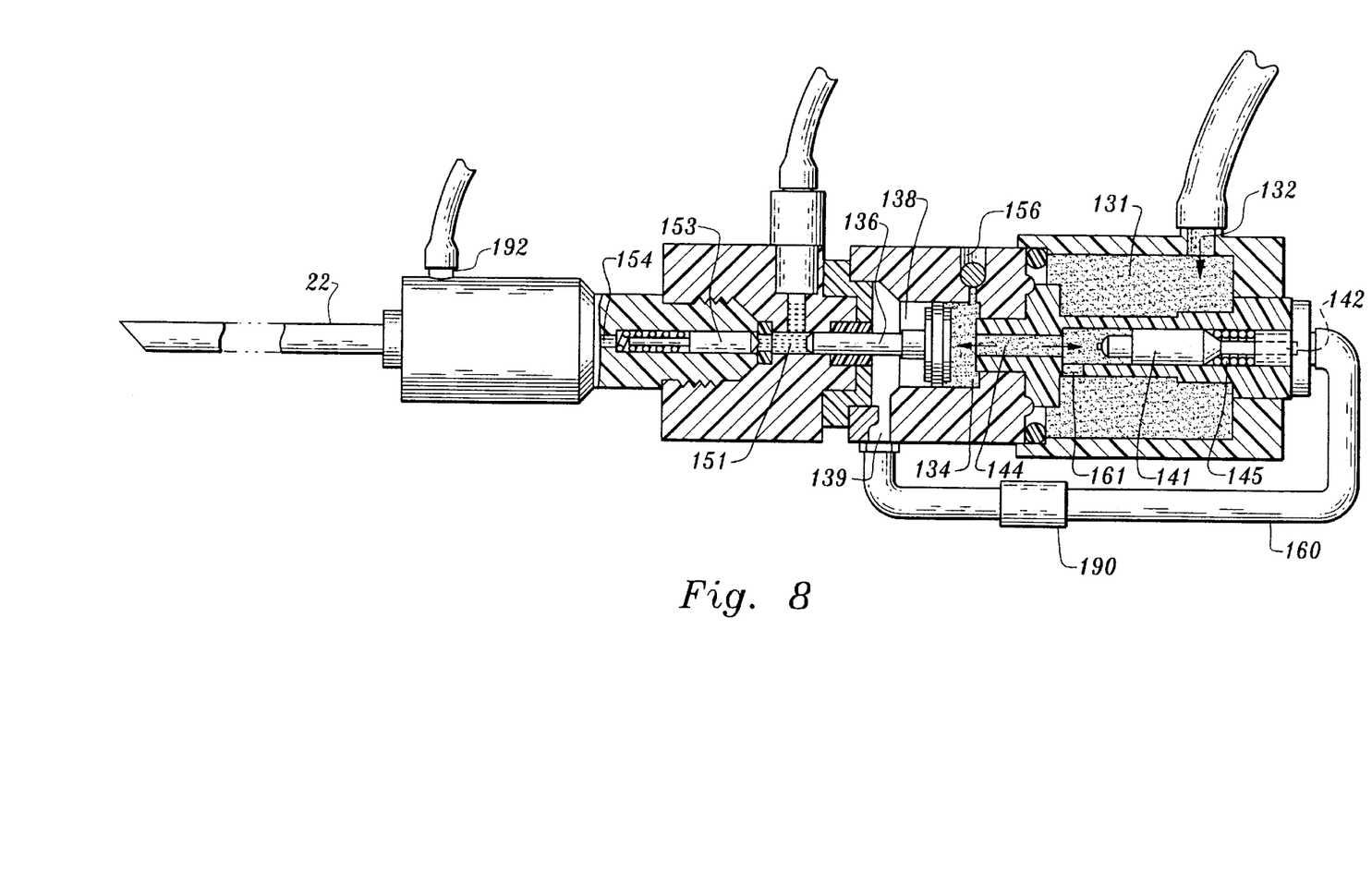
FIG. 8 is a cross-sectional view of the instrument of FIG. 7 as the pressure intensifier is activated.
Figure 14:
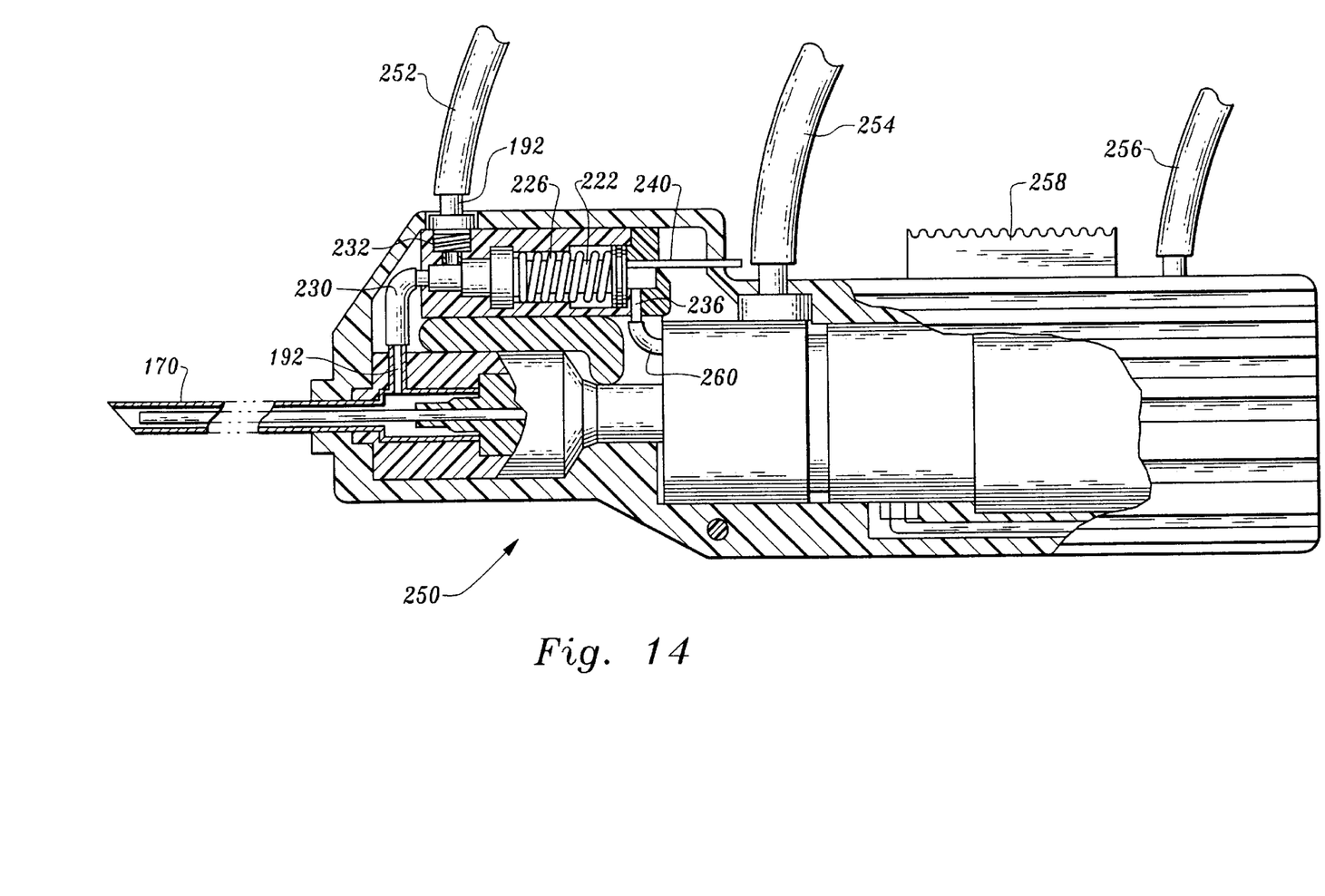
FIG. 14 is a cross-sectional view of a preferred embodiment of the present disclosure employing the pressure intensifier for fluid jet cutting and the suction device for aspiration.
Figure 15:
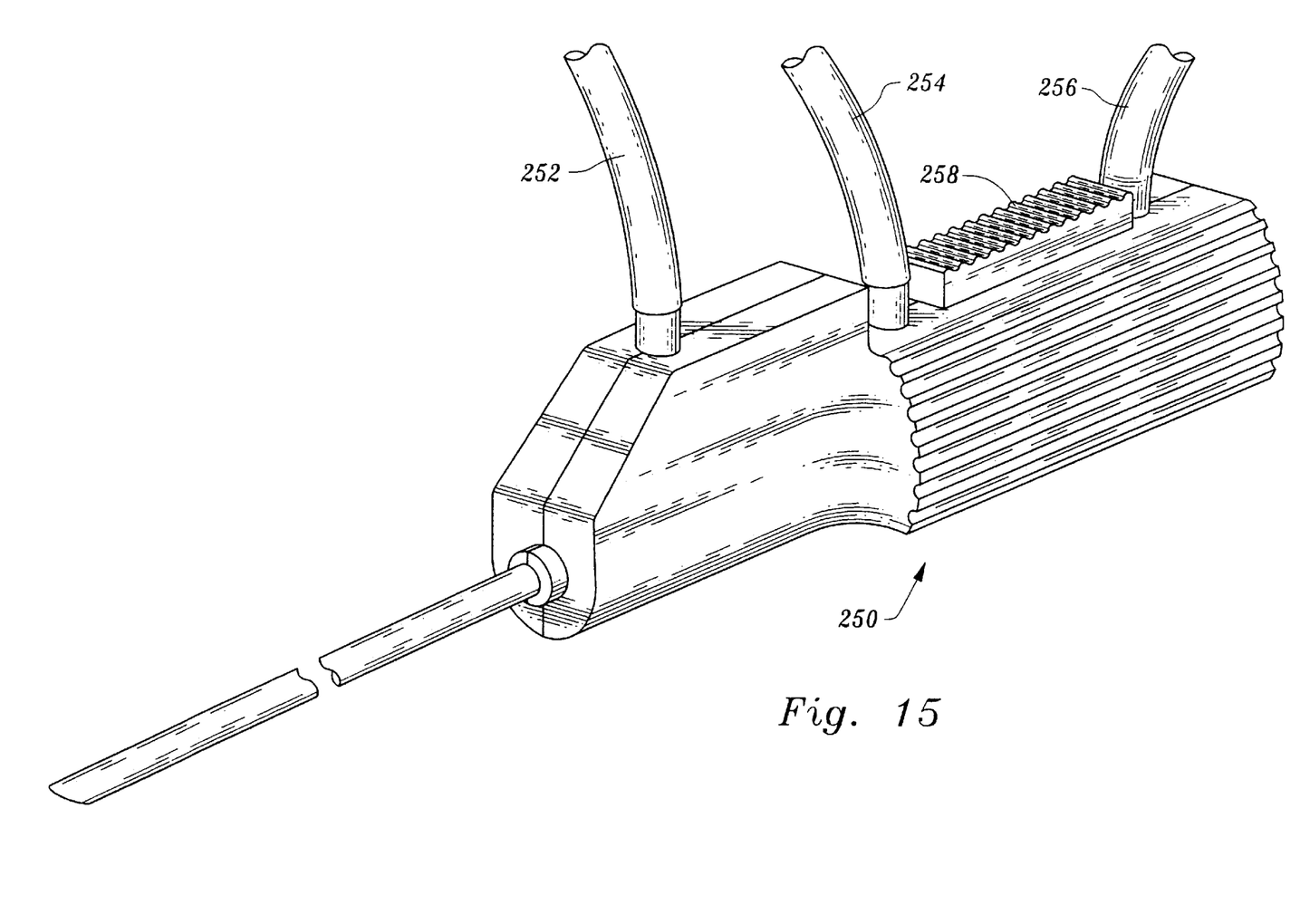
FIG. 15 is a perspective view of the instrument of FIG. 14.

FIGS. 14 and 15 illustrate an alternate embodiment of a handpiece to be incorporated into the fluid jet surgical instrument of the present disclosure. In accordance with this embodiment, the handpiece incorporates the suction device 220 of FIG. 11. The remaining components, e.g., the pressure intensifier mechanism, are substantially similar to the jet cutting instrument disclosed in FIGS. 7–10. With reference to FIGS. 14 and 15, in conjunction with FIGS. 7 and 11, handpiece 250 has a suction tube 252 connected to suction port 232 which supplies a continuous suction force provided by a remote suction source (not shown). Handpiece 250 further includes fluid tube 254 which is connected to check valve 157 (FIG. 7) and gas supply tube 256 which communicates with both gas port 236 (see also FIG. 11) via tube 260 and gas port 132 (FIG. 7). One skilled in the art can readily determine the mechanism required, such as a T-fitting or the like, for connecting the gas supply tube 256 with both gas port 236 and gas port 132. A trigger mechanism 258 is also provided to selectively actuate actuating valve 190 (FIG. 7) to vent retracting chamber 138 and bore 142 of the fluid intensifying mechanism and to actuate vent port 240. As seen in FIG. 14, suction tube 230 is connected to suction port 192 as seen in FIG. 7. The operation of handpiece 250 is similar to that described above with respect to FIGS. 7–12, and allows the operator to cut tissue with a fluid jet while at the same time providing for suction to aspirate excess fluid and emulsified tissue, while also providing for enhanced suction in the event a greater pressure is necessary or a blockage in cannula 170 occurs.

Although the subject disclosure has been described with respect to preferred embodiments, it will be readily apparent to those having ordinary skill in the art to which it appertains that changes and modifications may be made thereto without departing from the spirit or scope of the subject disclosure as defined by the appended claims.

What is claimed is:

1. A surgical instrument for aspirating fluid and debris from a surgical site, comprising
   a housing;
   cannula means extending from said housing;
   a suction source disposed in said housing for aspirating fluid and debris from said surgical site;
   a fluid port disposed on said housing for transporting aspirated fluid and debris from said housing, said suction source being disposed intermediate said cannula means and said fluid port;
   said suction source including vacuum generating means for creating a suction force at a distal end of said cannula means;
   a gas source connected to said instrument and a venting valve disposed in said housing; wherein said vacuum generating means comprises a piston member driven by said gas source and said venting valve, said gas source and said valve cooperating to reciprocatingly advance and retract said piston member;
   said vacuum generating means further including a biasing spring for retracting said piston member during venting of gas through said valve.

2. A surgical instrument for aspirating fluid and debris from a surgical site, comprising
   a housing;
   cannula means extending from said housing;
   a suction source disposed in said housing for aspirating fluid and debris from said surgical site;
   a fluid port disposed on said housing for transporting aspirated fluid and debris from said housing, said suction source being disposed intermediate said cannula means and said fluid port;
   a remote suction source;
   said fluid port including connection means for coupling said fluid port to said remote suction source, said remote suction source supplying a constant suction force to said cannula means, and said suction source disposed in said housing being adapted to selectively intensify said constant suction force;
   switch means for selectively energizing and de-energizing said suction source disposed in said housing;
   said suction source in said housing comprising a spring biased piston member disposed in a chamber, a first end of said chamber defining a driving chamber having a gas source and venting port, said gas source providing a force for driving said piston member against said spring, and said venting port being operable to release said gas force to permit said piston member to return to an at rest position under said spring biasing.

3. A surgical instrument according to claim 2, wherein a second end of said chamber defines a suction chamber, said piston member including a seal for creating a suction force as said piston member returns under said spring biasing.

4. A surgical instrument according to claim 3, wherein said housing includes means for delivering a source of irrigation fluid to said cannula.

5. A surgical instrument for aspirating fluid and debris from a surgical site, comprising:
   a housing;
   cannula means extending from said housing including a central passageway;
   means for generating a vacuum disposed in said housing and in fluid communication with said central passageway of said cannula means;
   a discharge port in fluid communication with said central passageway and said vacuum generating means for transporting aspirated fluid and debris from said housing;
   a suction source remote from said housing, said discharge port being in fluid communication with said remote suction source and said vacuum generating means;
   said remote suction source providing a constant suction force at a distal end of said cannula means, said vacuum generating means being adapted to selectively intensify said remote suction source;
   said vacuum generating means including switch means to selectively energize and de-energize said vacuum generating means;
   said vacuum generating means comprising a spring biased piston, said piston including sealing means for creating a suction force, said piston being gas driven to reciprocate within said housing;
   a chamber, said piston reciprocating in said chamber, said chamber including a drive portion including a port for said gas and a vent port, said chamber further including a suction portion in communication with said discharge port.

6. A surgical instrument according to claim 5, wherein said piston reciprocates in said chamber as said gas is charged into said drive portion and then vented from said vent port, said gas driving said piston against said spring, said spring returning said piston to an at rest position as said gas vents through said vent port.

7. A surgical instrument comprising:
   a low pressure suction source and a low pressure fluid source;
   a housing including connection means for coupling to the low pressure suction source and the low pressure fluid source;
   a cannula extending from said housing;
   a pressure amplifying means disposed within said housing;
   vacuum generating means disposed within said housing and in communication with the suction source;
   wherein said amplifying means generates a high pressure fluid output at a distal end of said cannula, and wherein said vacuum generating means amplifies a suction force generated by the suction source;
   said connection means connecting the fluid source with said pressure amplifying means and said vacuum generating means.

8. A surgical instrument according to claim 7, wherein said vacuum generating means comprises a piston member which defines at least a suction chamber and a driving chamber, said driving chamber being connected to said gas source and including a vent port, said gas source and vent port cooperating to reciprocate said piston member.

9. A surgical instrument according to claim 8, wherein said piston member includes a spring to bias said piston member towards said driving chamber, such that said gas source, said vent port and said spring cooperate to reciprocate said piston member.

10. A surgical instrument according to claim 9, wherein said piston member includes a sealing member for creating a suction force as said piston member reciprocates in said housing.

11. A surgical instrument according to claim 10, wherein said piston reciprocates in said chamber as said gas is charged into said drive chamber and then vented from said vent port, said gas driving said piston against said spring, said spring returning said piston to an at rest position as said gas vents through said vent port.

12. A surgical instrument according to claim 8, wherein said pressure amplifying means comprises a piston member which separates an interior of said housing into at least a driving chamber and a retracting chamber, said chambers being connected to said gas source to effect reciprocating motion of said piston member.

13. A surgical instrument according to claim 12, wherein said pressure amplifying means converts a low pressure fluid input from said fluid source into a high pressure fluid output through said cannula.

* * * * *